US00PP32162P3

(12) United States Plant Patent
Tufaro

(10) Patent No.: US PP32,162 P3
(45) Date of Patent: Sep. 8, 2020

(54) STRAWBERRY PLANT NAMED 'NSG 203'

(50) Latin Name: ***Fragaria* x *ananassa* Duchesne**
Varietal Denomination: NSG 203

(71) Applicant: Nova Siri Genetics S.r.l., Nova Siri (MT) (IT)

(72) Inventor: Nicola Tufaro, Nova Siri (IT)

(73) Assignee: NOVA SIRI GENETICS S.R.L., Nova Siri (MT) (IT)

( * ) Notice: Subject to any disclaimer, the term of this patent is extended or adjusted under 35 U.S.C. 154(b) by 0 days.

(21) Appl. No.: 16/501,366

(22) Filed: Apr. 1, 2019

(65) Prior Publication Data

US 2019/0307036 P1 Oct. 3, 2019

(30) Foreign Application Priority Data

Apr. 3, 2018 (QZ) ..... PBR 2018/0923

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./156, 208
See application file for complete search history.

*Primary Examiner* — Susan McCormick Ewoldt
*Assistant Examiner* — Karen M Redden
(74) *Attorney, Agent, or Firm* — Buchanan Ingersoll & Rooney P.C.

(57) ABSTRACT

A new and distinct variety of strawberry plant, referred to by its cultivar name, 'NSG 203', is provided which forms in abundance attractive early-season ripening large, medium red generally conical fruit having firm flesh that is longer than broad in configuration. A medium to high vigor is exhibited. The growth habit is dense, semi-upright and globose. White inflorescence is displayed. Commonly a calyx is displayed which is substantially bigger to the diameter of the corolla when open. The new variety is particularly well suited for the commercial industry.

15 Drawing Sheets

Figure 1:
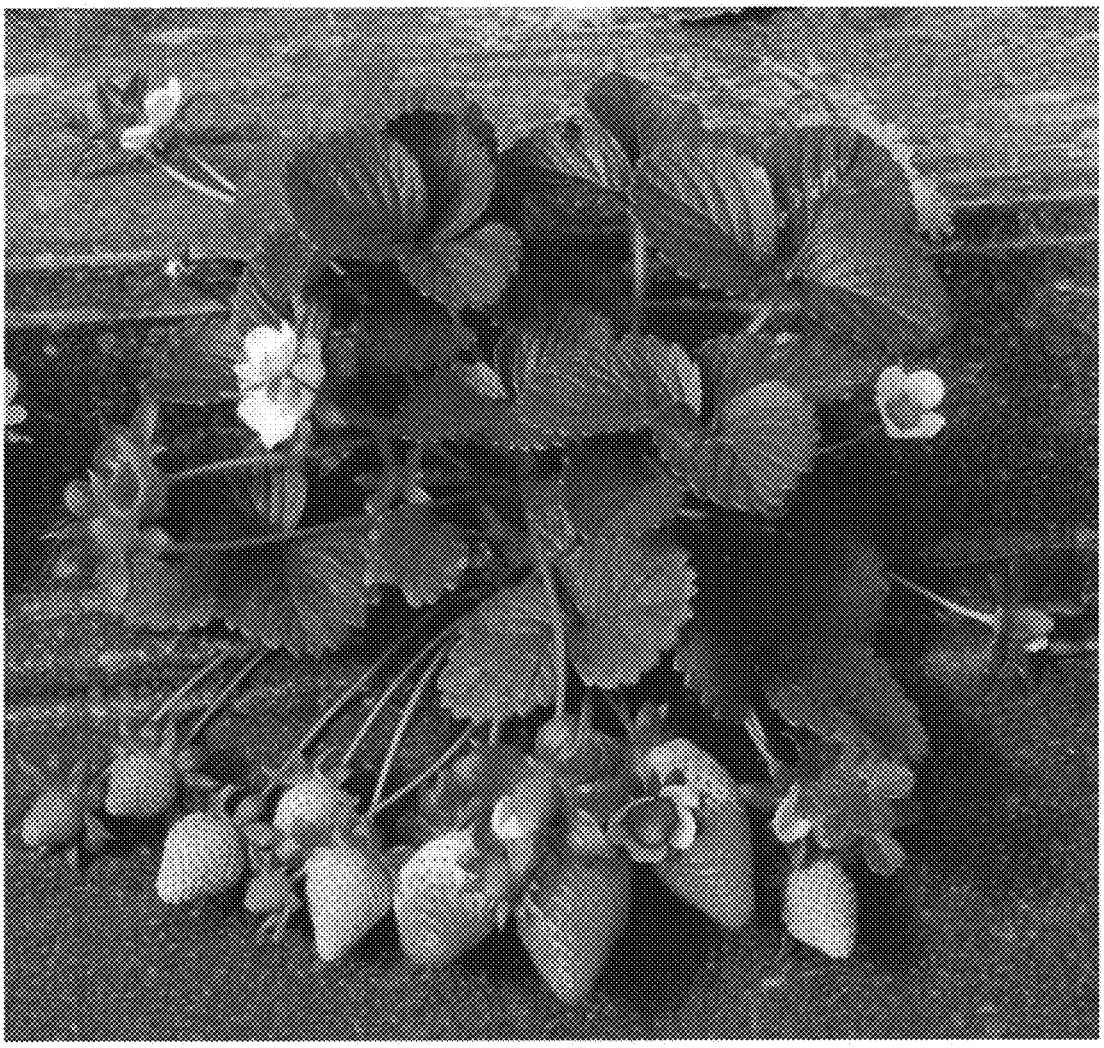

Botanical/commercial classification:
Latin name—*Fragaria* x *ananassa* Duchesne.
Varietal denomination: 'NSG 203'.

CROSS-REFERENCE TO RELATED APPLICATIONS

This application claims priority to Plant Breeder's Rights Application Number 2018/0923 which was filed in European Union through Community Plant Variety Office on Apr. 3, 2018, of which the content of is hereby expressly incorporated by reference in its entirety for all purposes.

SUMMARY OF THE INVENTION

The new and distinct short-day strawberry plant variety of the present invention was the product of a controlled breeding program that was carried out at Nova Siri (MT) Italy located at 40° 08' 40" N-16° 39' 40" E and 10 meters above sea level, wherein two parents were crossed which previously had been studied in the hope that they would contribute the desired characteristics. The female parent (i.e., the seed parent) was the CHARLENE variety (U.S. Plant Pat. No. 28,220 P3 and European Union Community Plant Variety Rights No. 45319), which is a strawberry short-day variety plant with medium-season yield and produces fruit with high contents of sugar. The male parent (i.e., pollen parent) was the NSG 1117 variety (non-patented in the United States and European Union Community Plant Variety Rights Application No. 2016/1694), which is a strawberry short-day variety with early-season ripening, produces big fruits, good yield and presents good tolerance to infection in plants by *Phytophthora cactorum* and *Colletotrichum acutatum*.

The parentage can be summarized as follows:

'CHARLENE' x 'NSG 1117'.

The seeds resulting from the above pollination were sown and small plants were obtained which were physically different from each other. Selective study and testing resulted in the identification of a single short-day strawberry plant of the new variety.

It was found that the new strawberry plant of the present invention possesses the following combination of characteristics:

(a) exhibits medium to high vigor and a dense, semi upright globose growth habit,
(b) displays, on an early basis, white inflorescence at a level generally above the foliage,
(c) commonly displays a calyx that is substantially bigger to the diameter of the corolla when open,
(d) forms in abundance attractive early-ripening large, medium red generally conical fruit having firm flesh that is longer than broad in configuration, and
(e) exhibits a good tolerance to infection by soil fungus.

The new variety well meets the needs of the horticultural industry. The new variety possesses characteristics that commonly are sought by commercial strawberry growers. For example, the new variety provides uniform attractive firm medium red early-ripening fruit in good yields. Accordingly, the new variety is to be freshly consumed and is considered promising for commercial introduction. The new variety requires an induction period for flowering. This may be achieved by growing in a colder climate away from the equator or at a higher altitude above sea level.

The new variety can be readily distinguished from its ancestors. More specifically, the 'CHARLENE' variety (i.e., the seed parent) displays generally conical shape fruit which is darker in external color compared to the generally conical, slightly rhomboid, shape fruit of the new variety. Specifically, 'CHARLENE' displays fruit with an external color commonly near Red Group 45B to Red Group 46A, whereas the new variety displays fruit with an external color commonly near Red Group 44A to Red Group 45B. Additionally, the 'NSG 1117' variety (i.e., the pollen parent) provides flowers which are smaller than the new variety. Specifically, the 'NSG 1117' variety exhibits flowers which are approximately 26 mm to 35 mm in diameter, whereas the new variety exhibits flowers which are approximately 37 mm to 47 mm in diameter.

Moreover, the new variety can be readily distinguished from non-parental related similar varieties. For example, the 'MELISSA' variety (U.S. Plant Pat. No. 28,081 P3 and European Union Community Plant Variety Rights No. 45318) provides shorter and fruit that is darker and slightly uneven in color compared to the fruit of the new variety. Specifically, 'MELISSA' provides fruit with a slightly uneven external color commonly near Red Group 45B to Red Group 46B, whereas the new variety provides fruit with an even external color commonly near Red Group 44A to Red Group 45B.

The new variety has been found to undergo asexual propagation in Poland and Italy by a number of routes, including by use of stolons and in vitro tissue culture. Specifically, the new variety has been asexually reproduced by the use of stolons at Zielona Gora-Ochla, Poland located at 51° 848 N-15° 447 E and at Nova Siri (MT) Italy by in vitro tissue culture. No rotting problems were observed on the roots during cultivation. The combination of characteristics exhibited by the new variety has been found to be stable and reliably transmitted to succeeding generations following such asexual reproduction. Accordingly, the new variety undergoes asexual propagation in a true-to-type manner by such asexual reproduction.

The new variety has been named 'NSG 203'. The new plant variety initially was designated as EE14 P 14 203.

BRIEF DESCRIPTION OF THE PHOTOGRAPHS

The accompanying photographs show, as nearly true as it is reasonably possible to make the same in color illustrations of this character, typical specimens of the new variety. The illustrated strawberry plants of the new variety were asexually reproduced by stolons during summer time in Ochla, Poland and were planted under the cover of plastic tunnels during mid-October 2017 at Nova Siri (MT), Italy.

FIG. 1—illustrates a semi-upright flowering plant on Feb. 10, 2018, where newly formed flowers are commonly disposed above the foliage and numerous early fruit are in the ripening process.

Figure 2:
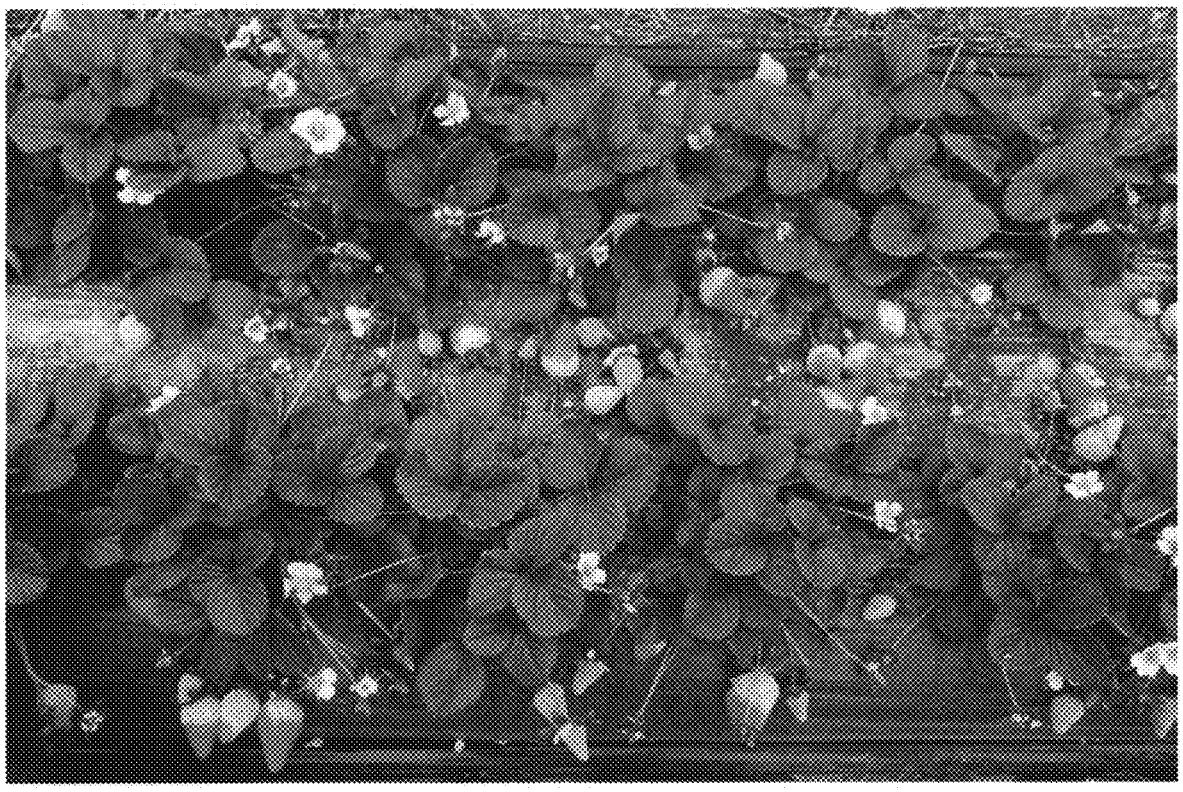

FIG. 2—illustrates a row of fruiting plants on Feb. 8, 2018, wherein uniform plants and abundant fruit production is apparent.

Figure 3:
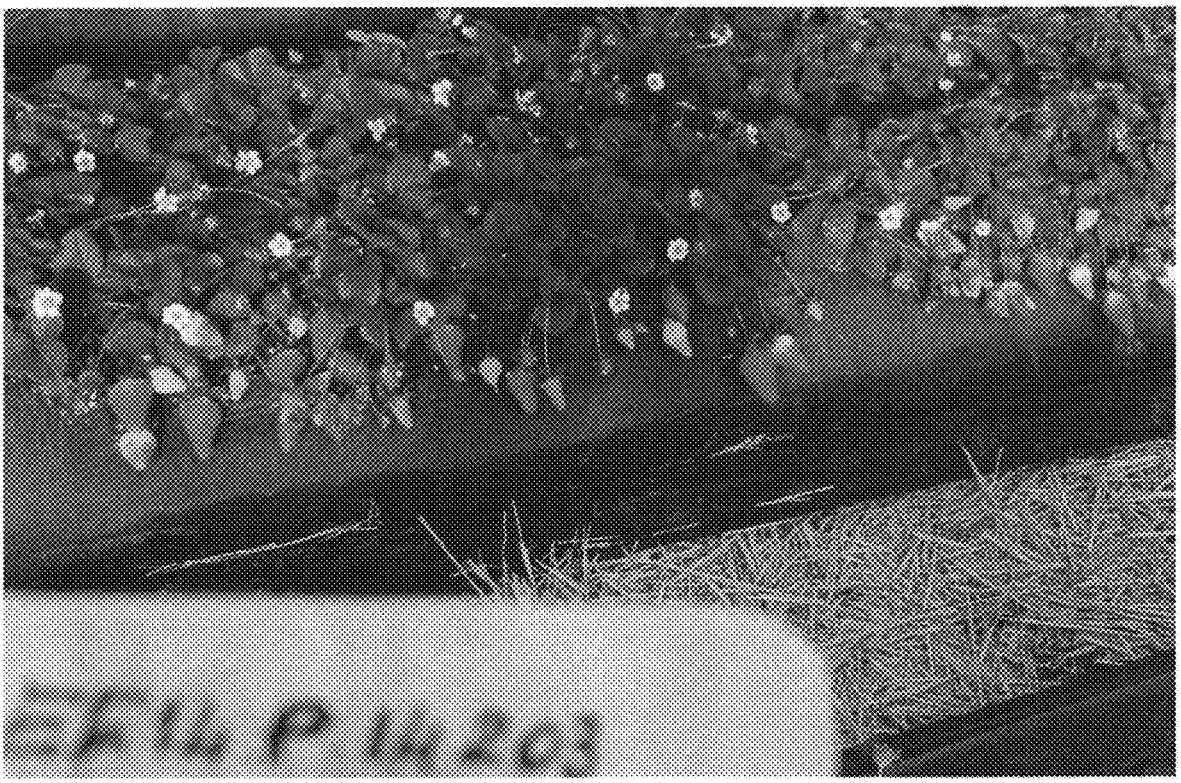

FIG. 3—illustrates a row of fruiting plants on Mar. 15, 2018, wherein medium to high vigor plants and uniform production in a successive formation of flowers and very uniform conical red fruits are present.

Figure 4:
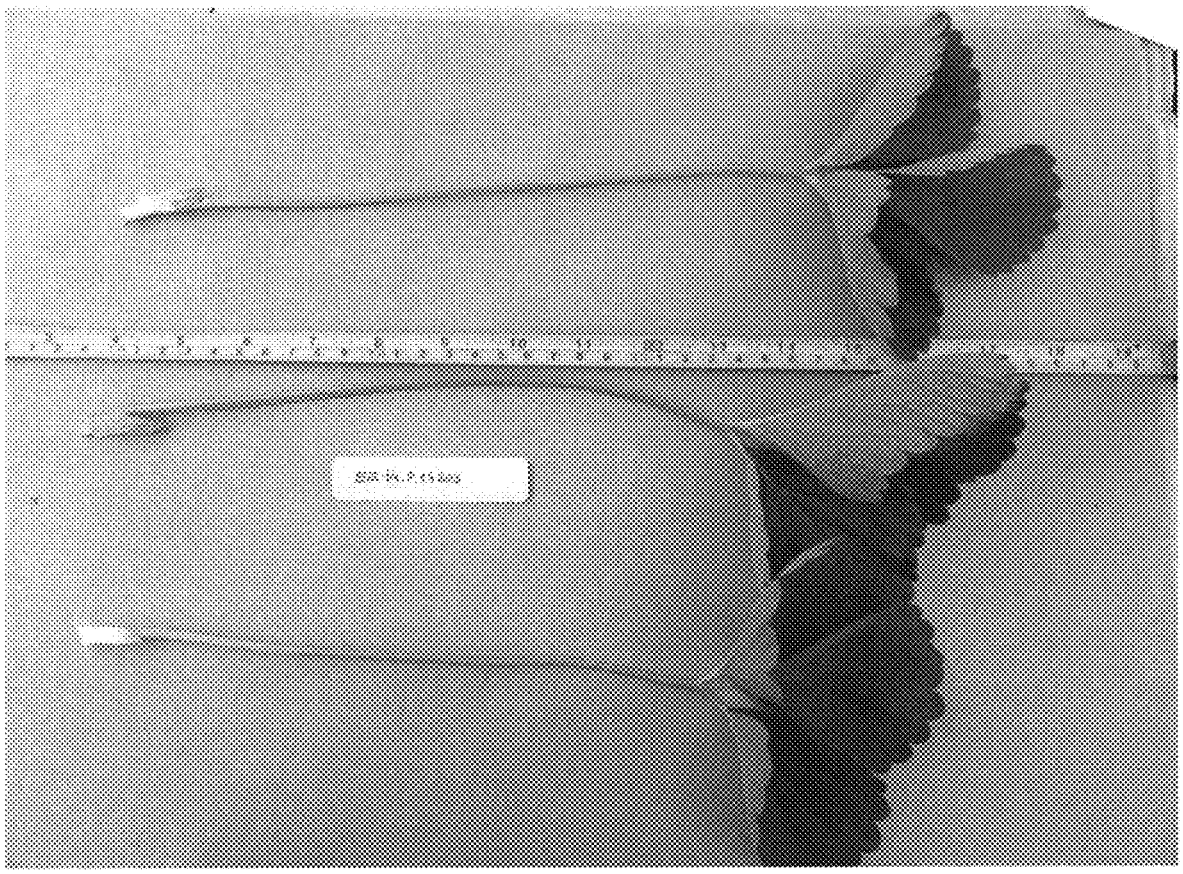

FIG. 4—illustrates specimens of three-leaflet leaves—whole leaves, wherein the petioles and stipules are further apparent (designate in images as EE14.P.14.203). Dimensions in centimeters and inches are included.

Figure 5:
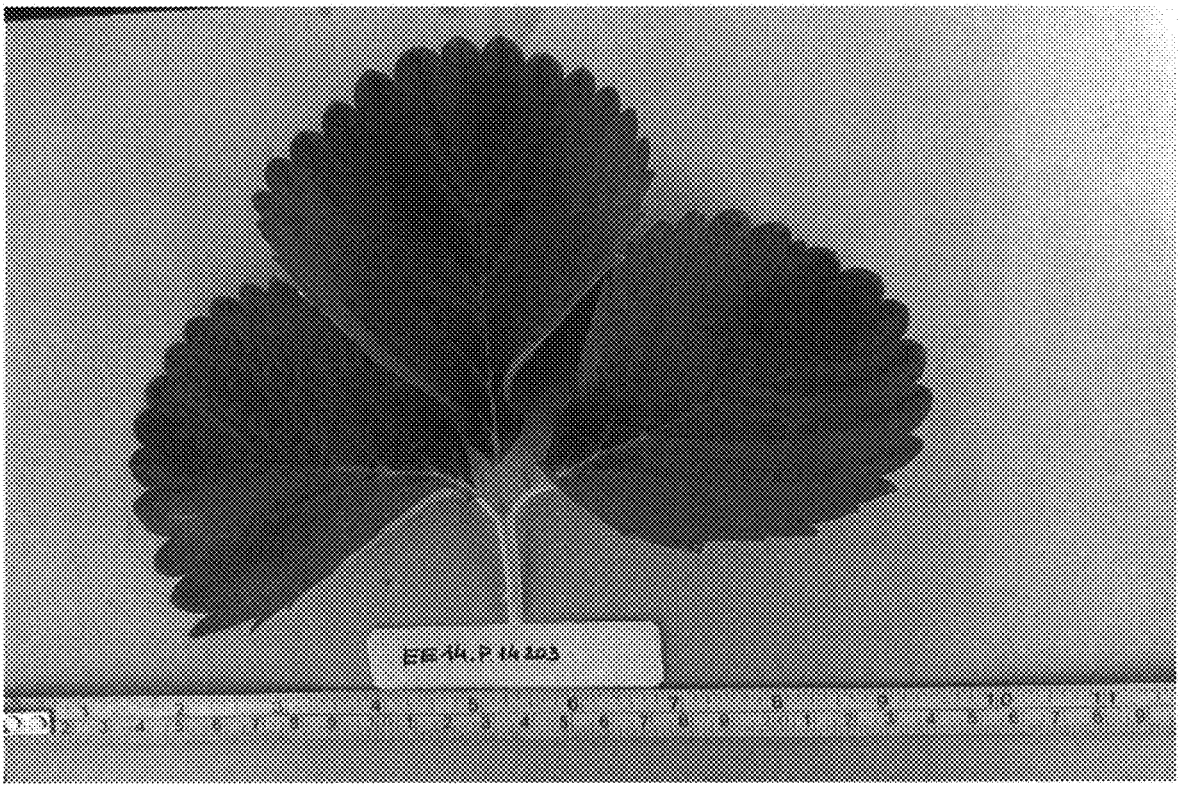

FIG. 5—illustrates a specimen of a typical three-leaflet leaf—upper surface (designate in image as EE14.P.14.203). Dimensions in centimeters and inches are included.

Figure 6:
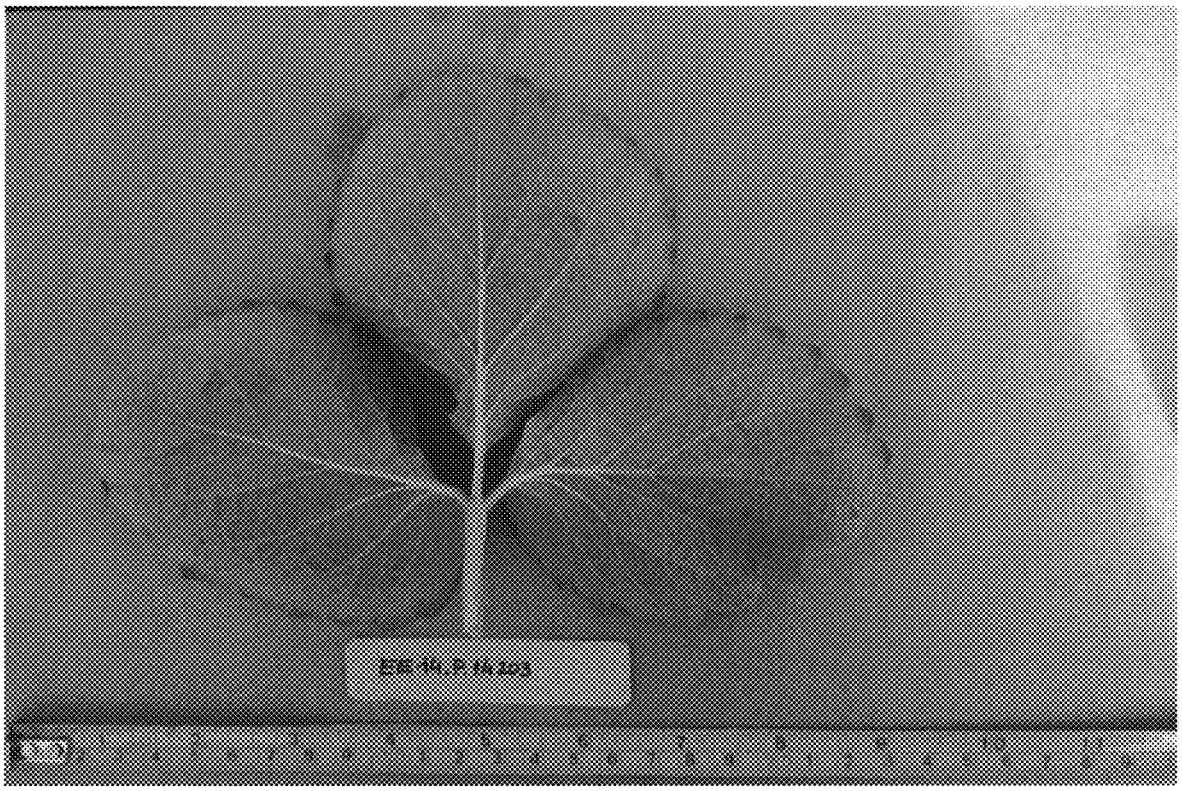

FIG. 6—illustrates a specimen of a typical three-leaflet leaf—under surface (designate in image as EE14.P.14.203). Dimensions in centimeters and inches are included.

Figure 7:
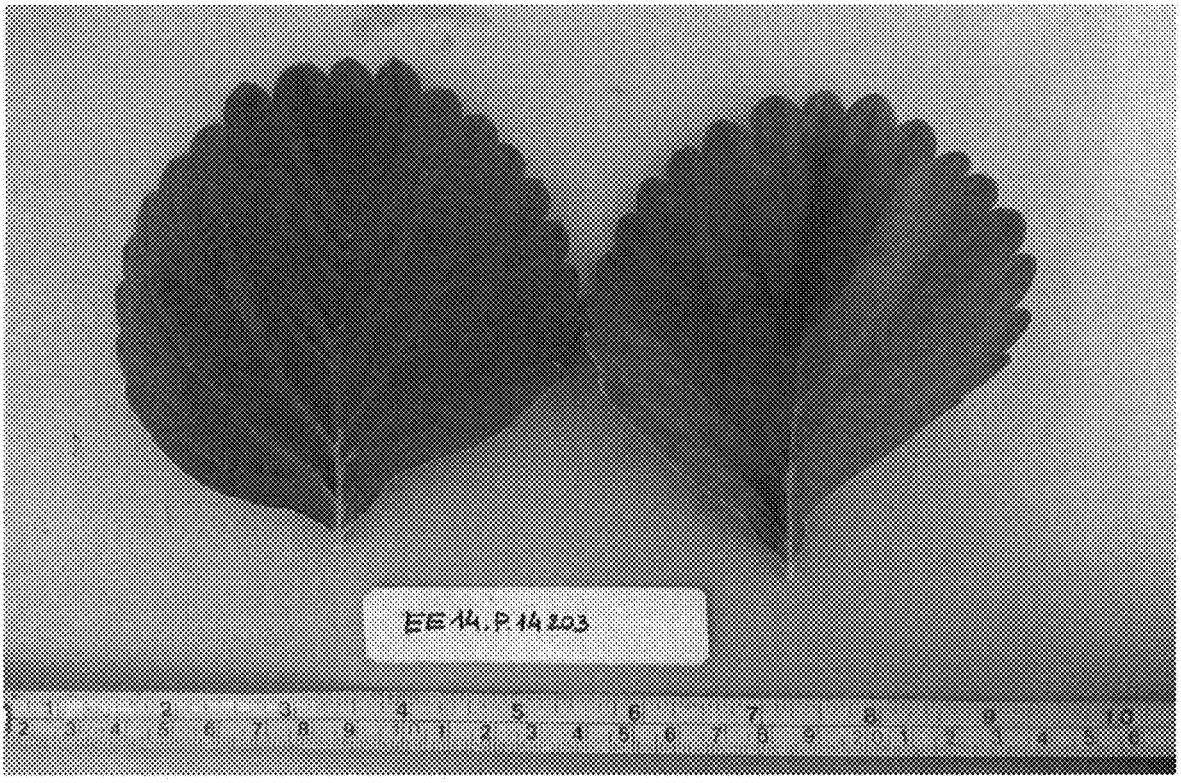

FIG. 7—illustrates a specimen of a terminal leaflet (left) and a lateral leaflet (right)—upper surface (designate in image as EE14.P.14.203). Dimensions in centimeters and inches are included.

Figure 8:
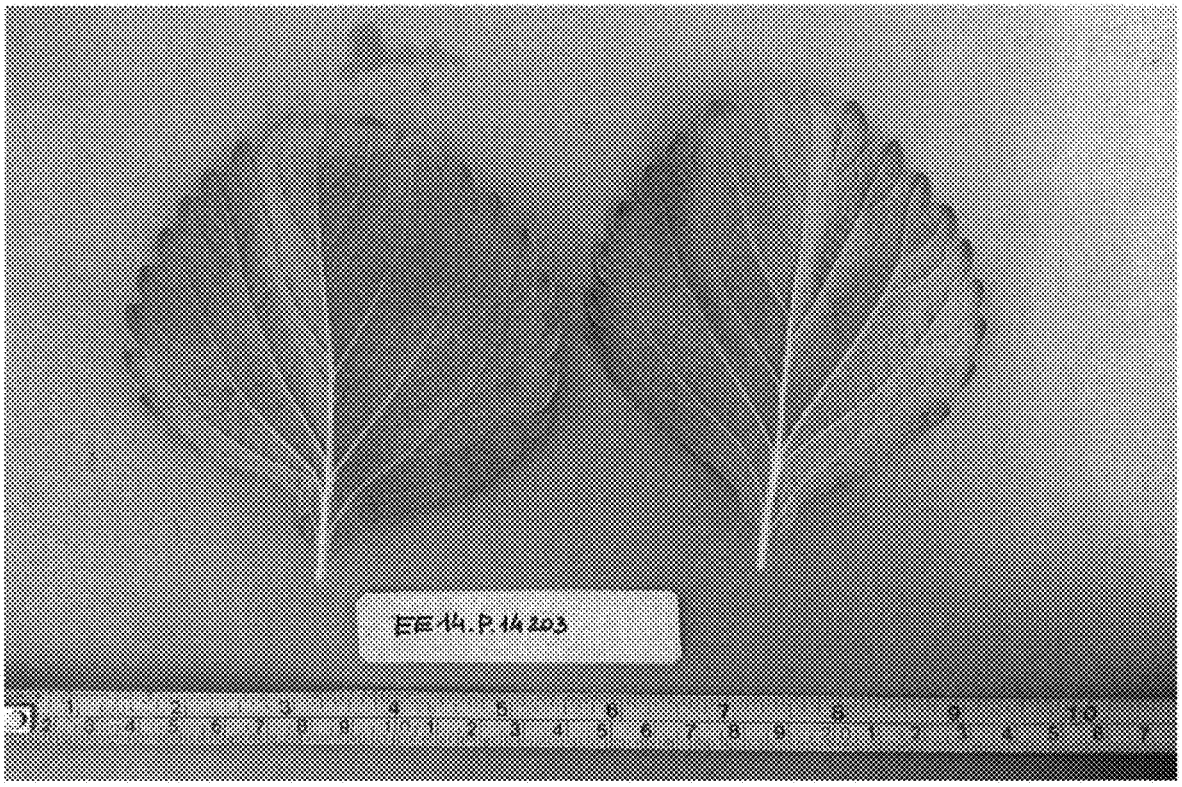

FIG. 8—illustrates a specimen of a terminal leaflet (left) and a lateral leaflet (right)—under surface (designate in image as EE14.P.14.203). Dimensions in centimeters and inches are included.

Figure 9:
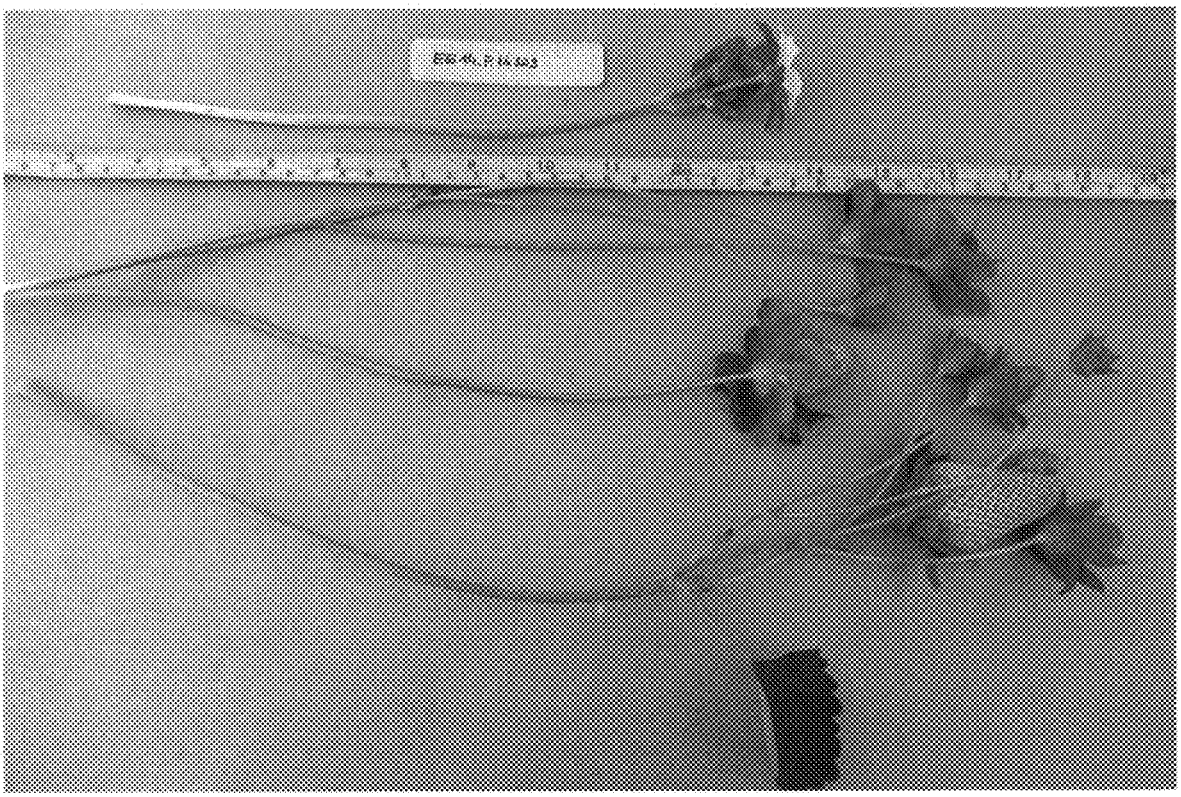

FIG. 9—illustrates a fruiting specimen (designate in image as EE14.P.14.203). Dimensions in centimeters and inches are included.

Figure 10:
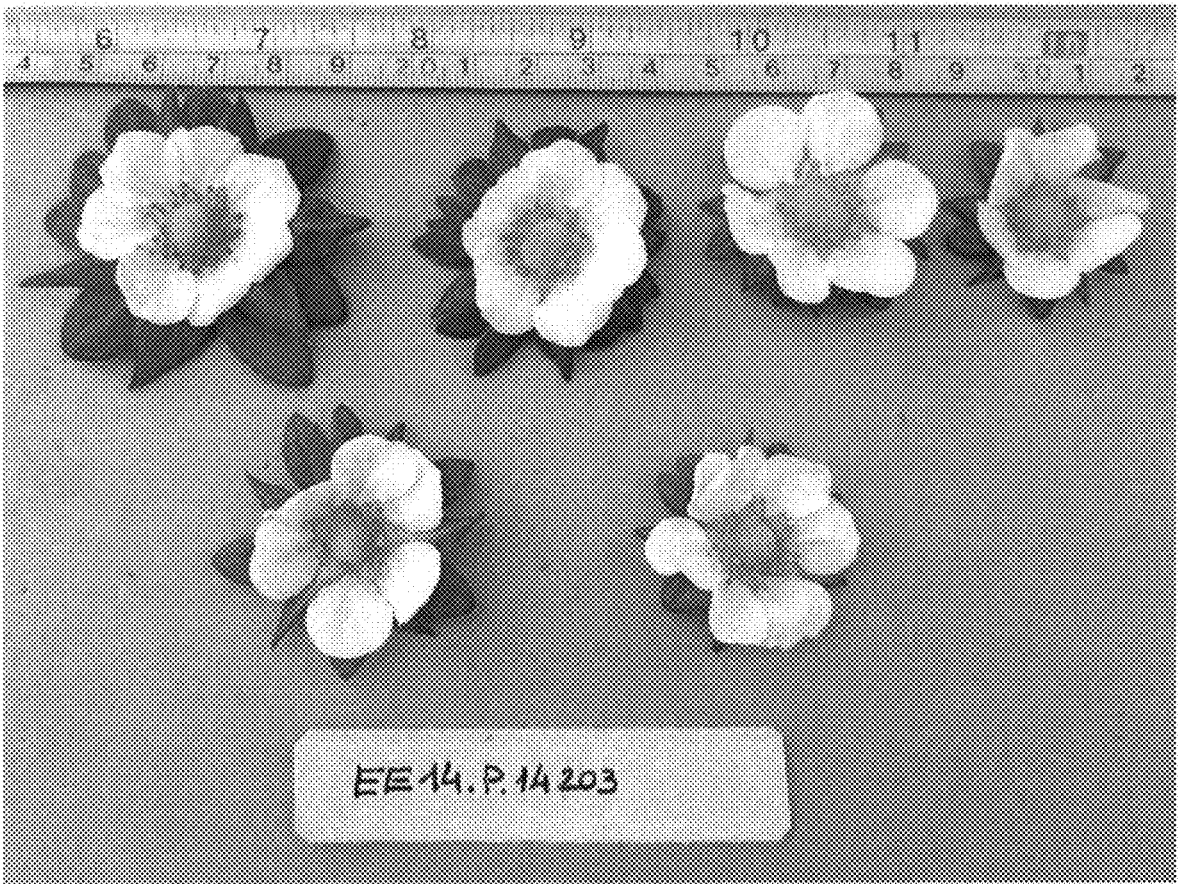

FIG. 10—illustrates specimens of corolla—top view, close view (designate in image as EE14.P.14.203). Dimensions in centimeters and inches are included.

Figure 11:
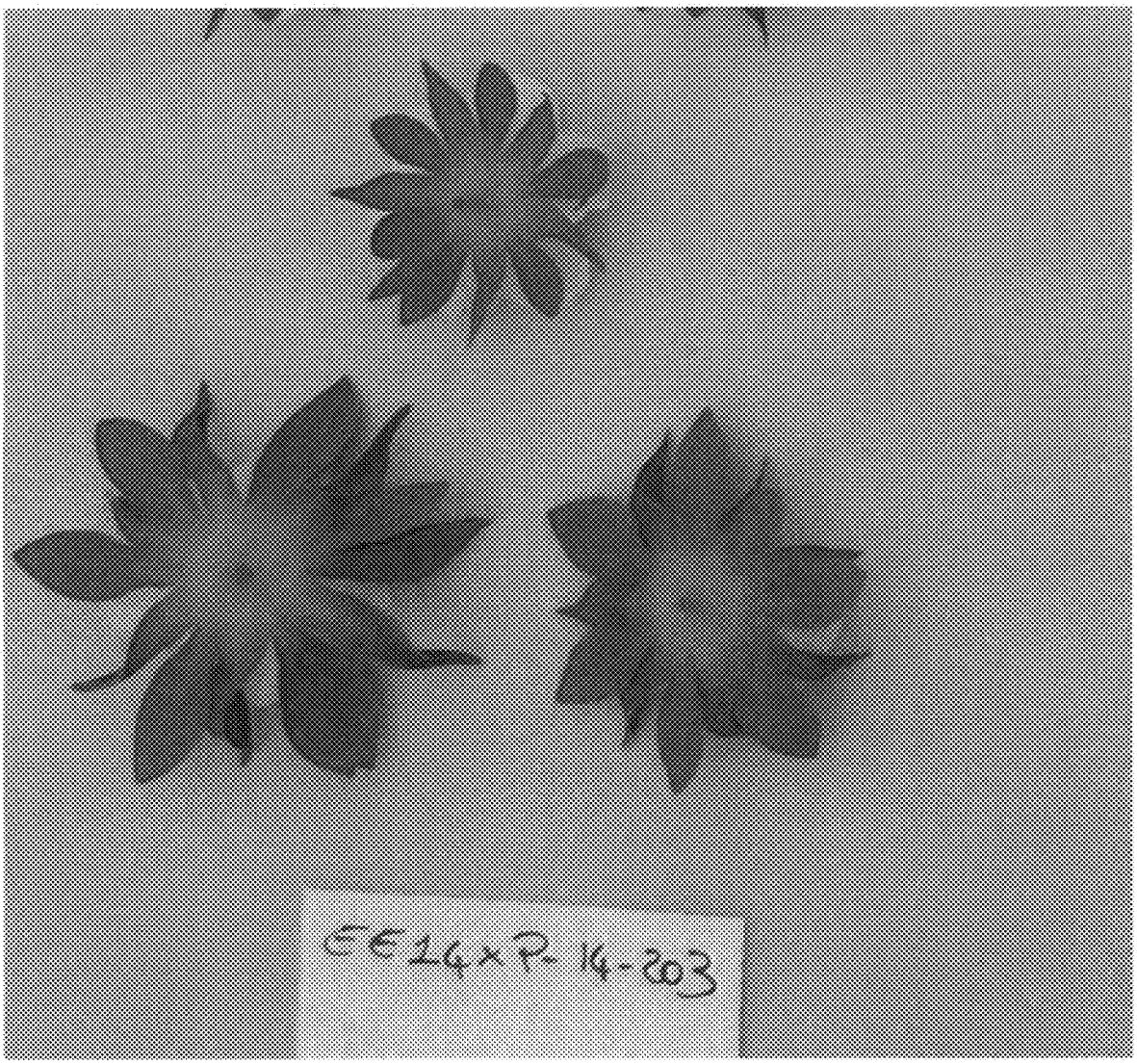

FIG. 11—illustrates specimens of calyx—under surface, close view (designate in image as EE14.P.14.203). Dimensions in centimeters and inches are included.

Figure 12:
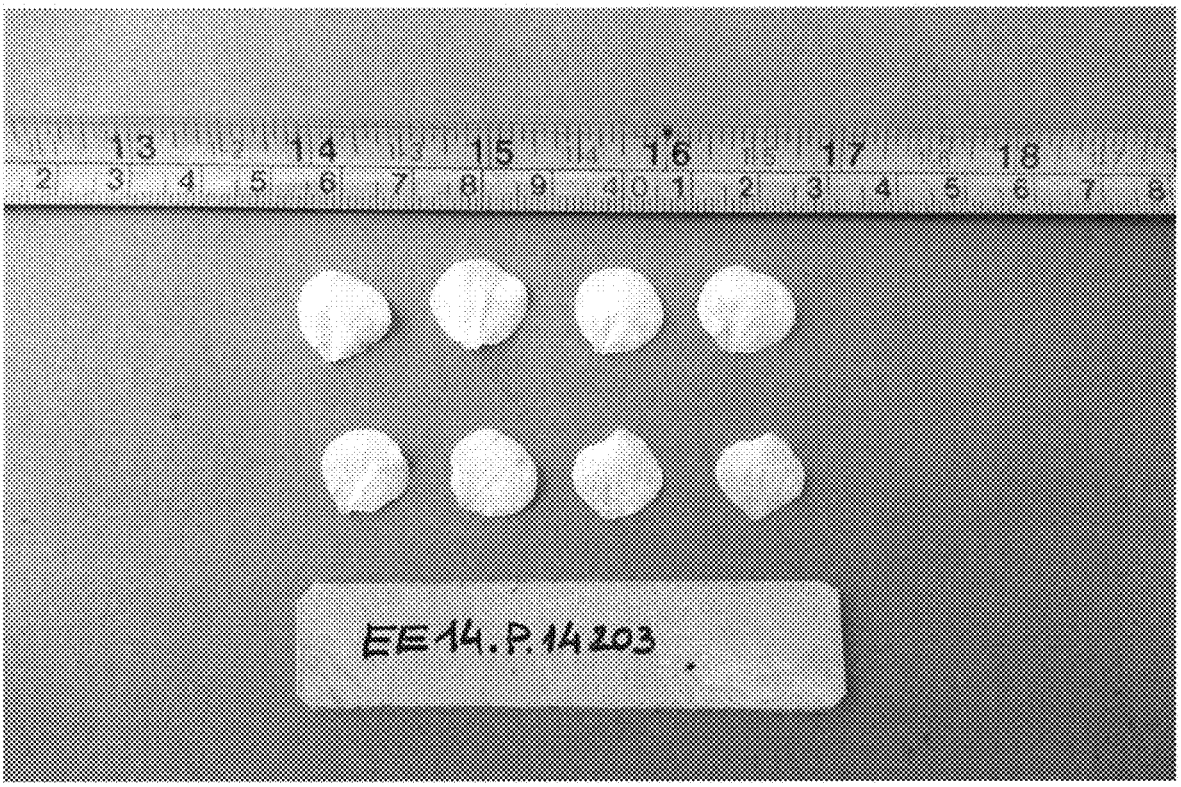

FIG. 12—illustrates specimens of petals of the flowers (designate in image as EE14.P.14.203). Dimensions in centimeters and inches are included.

Figure 13:
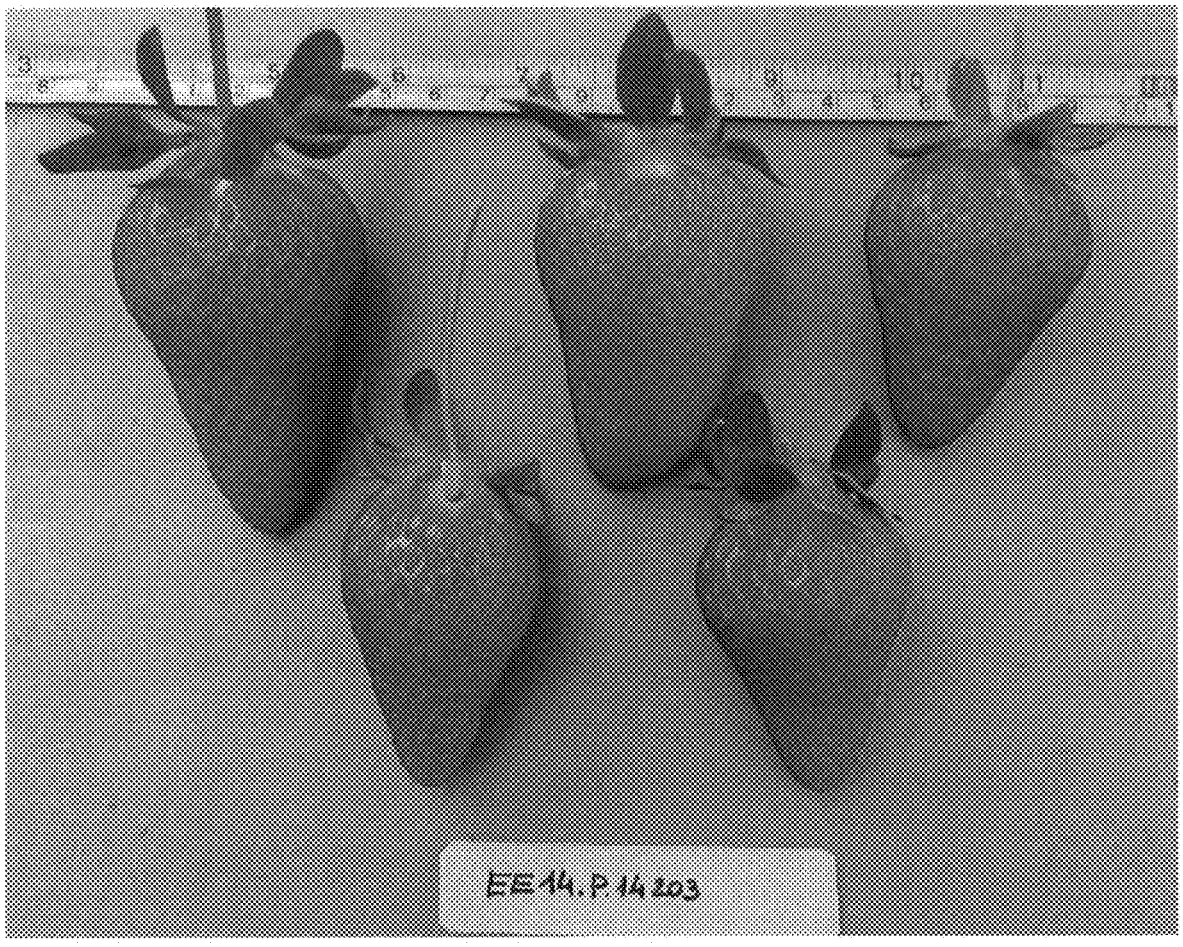

FIG. 13—illustrates specimens of mature fruit—whole (designate in image as EE14.P.14.203). Dimensions in centimeters and inches are included.

Figure 14:
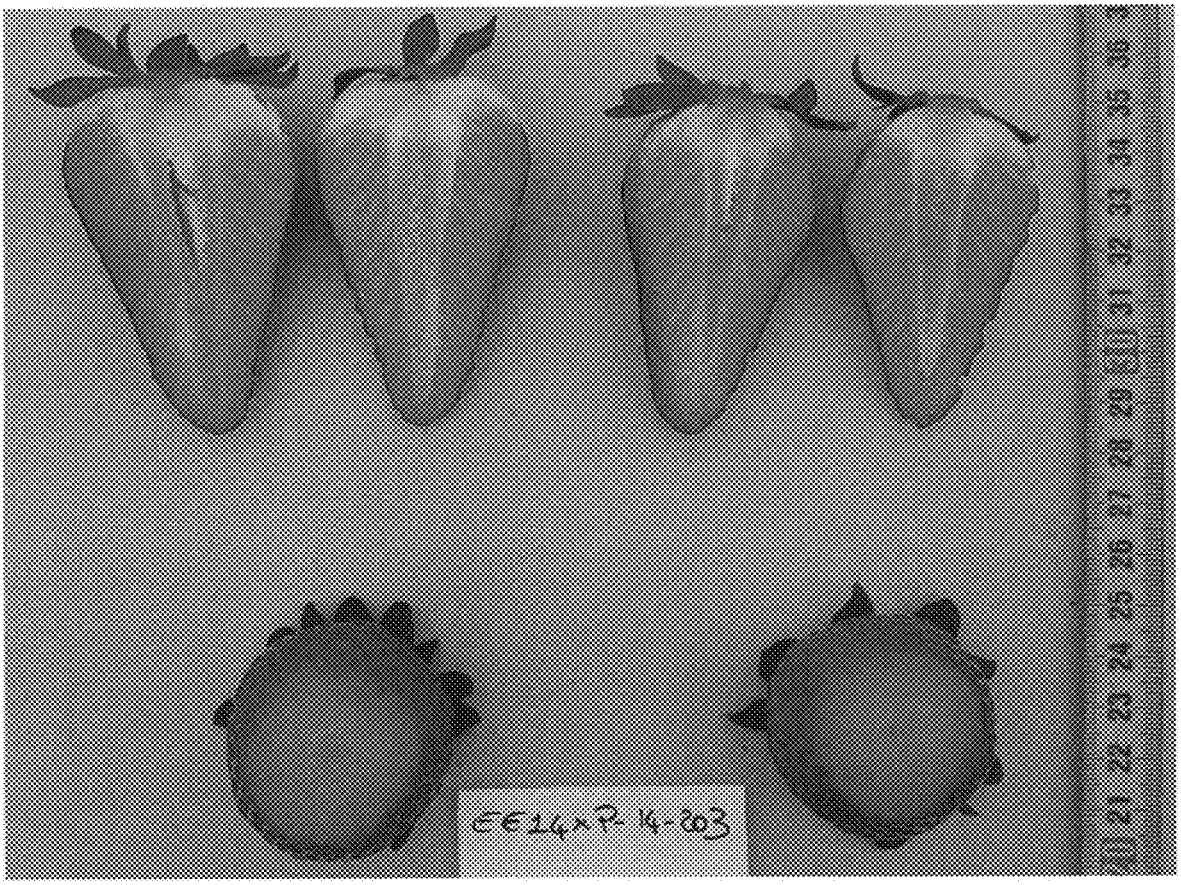

FIG. 14—illustrates specimens of mature fruit—internal sections (designate in image as EE14.P.14.203). Dimensions in centimeters and inches are included.

Figure 15:
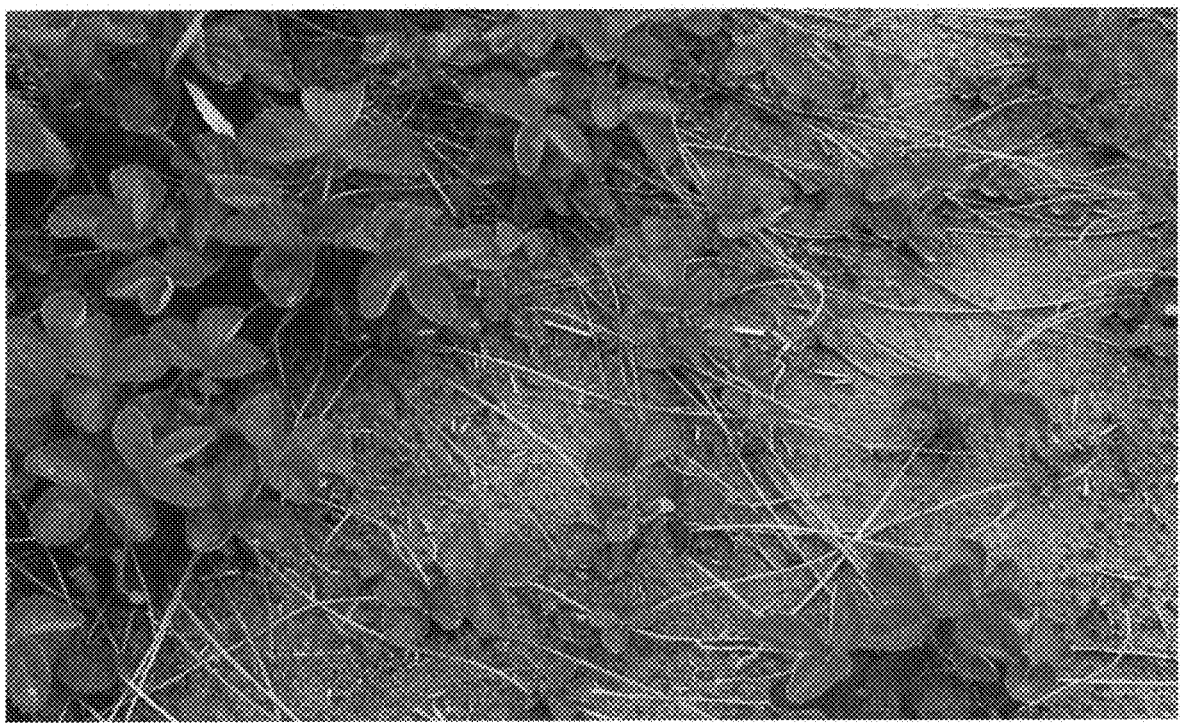

FIG. 15—illustrates specimen of runners (stolons) on Aug. 15, 2018.

DETAILED BOTANICAL DESCRIPTION

The chart used in the identification of colors is that of The Royal Horticultural Society ("R.H.S." Colour Chart), London, England, Edition V. The terminology which precedes reference to the chart has been added to indicate the corresponding color in more common terms. The detailed botanical description is based on plants which were reproduced asexually by the use of stolons at Zielona Gora-Ochla, Poland (located at 51° 848 N-15° 447 E), transplanted at Nova Siri (MT), Italy (located at 40° 08' 40" N-16° 39' 40" E and 10 meters above sea level) in October and growing under the cover of plastic tunnels.

With regard to stolons, their description took place in Poland. These stolons are derived from frigo plants transplanted in Poland at Zielona Gora Ochla in April. Therefore the age of the plants on which the botanical description was made is between two and eight months from the transplants.

Plant:

*Type*.—Short-day.

*Configuration*.—Semi-upright and dense.

*Vigor*.—Medium to high.

*Leaf*.—Approximately 23 cm to 33 cm in length on average, including the petiole.

*Leaflets*.—Number: commonly 3. — size: medium in size, approximately 9 cm to 10.5 cm in length on average for terminal leaflets, and approximately 8.5 cm to 9.5 cm in width on average for terminal leaflets. — terminal leaflet: commonly moderately longer in length than width, possesses a concave cross-section, a crenate margin, and an obtuse base. — blistering: commonly is weak to medium in quantity. — glossiness on the upper surface: medium. — color: variegated coloration commonly is absent; upper surface coloration commonly being near Green Group N141A to Green Group N141B; and under surface commonly being near Green Group 138C to Green Group 139C. — texture (upper surface): wrinkled, waxy puncture, not dense, presence of trichomes all over the surface. — texture (lower surface): general roughness, trichomes mainly present on the ribs. — venation: with respect to the main grain of each individual leaf, the main transverse ribs are grafted forming an acute angle and the curvature of the main transversal rib is more evident starting from its median zone.

*Stolons*.—High in quantity, some weak anthocyanin coloration of commonly near Red-Purple Group 65C to Red-Purple Group 65D, and the distance between plants rooted in the same stolon is approximately 35 cm to 43 cm on average.

*Petioles*.—Medium to long, approximately 18 cm to 23 cm in length on average, the average minor axis and the average major axis measured at approximately 3 cm from the base of the stipule are approximately 2.7 mm and 3.3 mm, respectively, color is commonly near Yellow-Green Group N144C to Yellow-Green Group N144B, and commonly bear generally horizontally disposed fine pubescence.

*Stipules*.—Approximately 2.2 cm to 3.1 cm in length on average, average width of a closed stipules is approximately 9.4 mm, average width of open stipules is approximately 21.8 mm and the color is Yellow-Green Group 145 B, which commonly bears some weak anthocyanin coloration of near Red-Purple Group 68D to Red-Purple Group 69A.

*Floral fragrance*.—Slightly present.

Inflorescence:

*Flowering time*.—Early, second/third week of December in Nova Siri (MT), Italy (10 meters above sea level).

*Flower disposition*.—Generally slightly above the foliage.

*Flower number*.—Medium, commonly 4 to 6.

*Pedicel hairs*.—Pubescence generally disposed somewhat upwards.

*Pedicel length*.—The average length of the main and secondary pedicles measured from the base of the calyx, with the first fruit already ripe on the main axis is approximately 12 cm.

*Pedicel diameter*.—Measured at approximately 3 cm from the calyx, diameter is approximately 2.2 mm.

*Pedicel color*.—Commonly near Yellow-Green Group 144C to Yellow-Green Group 144D.

*Flower size*.—Medium to large, with primary flowers approximately 3.7 cm to 4.7 cm in diameter on average, and secondary flowers approximately 3.0 cm to 4.2 cm in diameter on average, commonly the open calyx is substantially larger in diameter than the diameter than the corolla.

*Petals*.—Number: approximately 6 to 8 on average. — arrangement and shape: overlapping, somewhat rounded overall, commonly the length is equal to the width, and rounded apex. — size: approximately 1.2 cm to 1.3 cm on average in length and width on average; approximately 1.4 cm on average in length and width in primary flowers and approximately 1.1 cm in length and width in secondary flowers. — color: commonly near White Group N155C. — texture (upper surface): spongy texture, smooth surface, glabrous, with small translucent points, quite evident ribs. — texture (lower surface): slight general roughness, glabrous surface, slightly pinched.

*Stamens*.—Average number is approximately 30, average length is approximately from 4 mm to 5 mm, the color of the filament is Yellow Group 2 C.

*Anthers*.—Number is approximately 26 to 30 on average, commonly disposed below the pistils, and color is commonly near Yellow Group 9A to Yellow Group 9B.

*Pollen*.—In abundance.

*Stigma*.—Cylindrical fan, average aperture of approximately 320 μm, dry, waxed, not feathery.

*Style*.—average length approximately between 1600 μm to 1800 μm, average diameter of 220 μm, which thins at the level of insertion on the ovary, entirely crossed by a stylus channel with an average diameter of approximately 42 μm, Gynobasic style.

*Ovary*.—Superior, oval shape and average major axis and the average minor axis of approximately 770 μm and 510 μm.

*Sepals*.—Shape: generally lanceolate in configuration, generally somewhat outwardly disposed. — number: approximately 12 to 14 on average. — size: approximately 1.5 cm to 2.4 cm in length on average, and approximately 5 mm to 8 mm in width on average at the broadest point. — color: the upper surface is commonly near Green Group 143C to Green Group 143D and the under surface is commonly near Green Group 141C. — texture (upper surface): smooth with slight waxy marks and trichomes at the edge. — texture (lower surface): slightly wrinkled with presence of trichomes mainly on the basal part.

Fruit:

*Bearing*.—Non-remontant.

*Timing*.—Early fruiting commonly with approximately 25 to 30 days from first blooming to first fruit ripening.

*Shape*.—Generally conical, slightly rhomboid, longer than broad, commonly with a slight difference between terminal and other fruits.

*Size*.—Medium to large, with the primary fruit approximately 6.0 cm to 7.2 cm in length on average; approximately 3.9 cm to 4.2 cm in width on average at the broadest point; and approximately 23 grams on average.

*Surface*.—Generally smooth texture with strong glossiness.

*External color*.—Substantially uniform commonly near Red Group 44A to Red Group 45B.

*Internal color*.—Flesh is commonly near Red Group 40A to Red Group 41B, and the core is commonly near Orange-Red Group 34A to Orange-Red Group 32A.

*Firmness*.—Firm to very firm.

*Cavity*.—Absent or small fruit cavity, as illustrated in FIG. 14.

*Achenes*.—located generally below the fruit surface and cover nearly the entire fruit surface commonly with only a very narrow band (if any) where achenes are absent, and commonly going from near Orange Group 25B to Red Group 45B in coloration.

*Calyx*.—Commonly the fruit is raised at the point of attachment, the calyx commonly attaches to the fruit with strong adherence, the sepals are disposed generally outwards, and the calyx diameter when open in relation to diameter of fruit is commonly slightly bigger.

*Peduncle*.—Long, approximately 25 cm to 38 cm in length on average for primary fruit, the average minor axis and the average major axis measured at approximately 3 cm from the base in cross section are approximately 3 mm and 3.4 mm, respectively, and color is commonly near Yellow-Green Group N144B to Yellow-Green Group 144C.

*Pedicel*.—Commonly with pubescence extending upwards, and color is commonly near Yellow-Green Group N144C

*Storability*.—Medium.

Development:

*Fertilization*.—Self-fertile.

*Resistance to disease*.—During observations to date, the fruit of the new variety has shown mild sensitivity to Powdery Mildew after a rain period, no sensitivities to any other diseases were observed.

*Winter hardiness/color tolerance*.—Unknown.

*Drought/heat tolerance*.—Good.

Plants of the 'NSG 203' variety have not been observed under all possible environmental conditions to date. Accordingly, it is possible that the phenotypic expression may vary somewhat with changes in light intensity and duration, cultural practices, and other environmental conditions.

SUPPLEMENTAL COMPARATIVE DATA

Hereafter, additional comparative fruit data is provided for the new variety, the 'CHARLENE' variety (i.e., the female variety), the 'NSG 1117' variety (i.e., the male parent), and the 'MELISSA' variety. The plants were asexually reproduced by the use of stolons in 2017 at Zielona Gora-Ochla, Poland located at 51° 848 N-15° 447 E, and planted in field on Oct. 15, 2017. All varieties were grown under the cover of plastic tunnels at Nova Siri (MT) Italy located at 40° 08' 40" N-16° 39' 40" E (10 meters above sea level). The fruit were first picked on January 12 and last picked on May 30. The fruit were evaluated and compared on the dates indicated. Average data is as follow:

TABLE 1

Accumulated Production of First Quality Fruit (g/plant) On year 2018 at Nova Siri - Italy

| Plant | February 30th | March 30th | April 30th | May 20th |
|---|---|---|---|---|
| 'NSG 203' | 70 | 296 | 657 | 754 |
| 'CHARLENE' | 45 | 170 | 390 | 595 |

TABLE 1-continued

Accumulated Production of First Quality Fruit (g/plant) On year 2018 at Nova Siri - Italy

| Plant | February 30th | March 30th | April 30th | May 20th |
|---|---|---|---|---|
| 'NSG 1117' | 24 | 195 | 405 | 600 |
| 'MELISSA' | 73 | 227 | 478 | 672 |

TABLE 2

Overall Comparison of Average Fruit Weigh in Nova Siri - Italy on year 2018

| Plant | g/fruit |
|---|---|
| 'NSG 203' | 23 |
| 'CHARLENE' | 22 |
| 'NSG 1117' | 24 |
| 'MELISSA' | 26 |

TABLE 3

Average Fruit Weight on Specified Dates

| Plant | March 30th (grams) | April 30th (grams) | May 18th (grams) |
|---|---|---|---|
| 'NSG 203' | 25 | 23 | 22 |
| 'CHARLENE' | 24 | 22 | 19 |
| 'NSG 1117' | 25 | 24 | 23 |
| 'MELISSA' | 25 | 26 | 22 |

TABLE 4

Fruit Analysis on May 30, 2018

| | 'NSG 203' | 'CHARLENE' | 'NSG 1117' | 'MELISSA' |
|---|---|---|---|---|
| Firmness (average)* | 0.75 | 0.74 | 077 | 0.75 |
| Dry Matter (%)** | 8.24 | 8.50 | 8.25 | 8.25 |
| pH (to 20°) | 3.40 | 3.80 | 3.60 | 3.93 |
| Acidity as Anhydride Citric (%) | 0.83 | 0.70 | 0.69 | 0.60 |
| Soluble Solids (% Brix) | 8.00 | 8.80 | 7.60 | 9.00 |
| Maturity Index*** | 9.70 | 12.57 | 11.01 | 15.00 |

*Resistance to penetration measured in kilograms using a Turoni (Italy) pentrometer (20 Kg × 0.01).
**Weight of residue from the titration of the fruit after drying at 103° C. until is achieved a constant weight.
***Relation between soluble solids and acidity as acetic anhydride.

I claim:

1. A new and distinct strawberry plant characterized by the following combination of characteristics:

(a) exhibits medium to high vigor and a dense, semi upright globose growth habit, (b) displays, on an early basis, white inflorescence at a level generally above the foliage, (c) commonly displays a calyx that is substantially bigger to the diameter of the corolla when open, (d) forms in abundance attractive early-ripening large, medium red generally conical fruit having firm flesh that is longer than broad in configuration, and (e) exhibits a good tolerance to infection by soil fungus; substantially as herein shown and described.

* * * * *